United States Patent
Kesner

(10) Patent No.: US 9,767,536 B2
(45) Date of Patent: Sep. 19, 2017

(54) MEDICAL IMAGING

(71) Applicant: Memorial Sloan-Kettering Cancer Center, New York, NY (US)

(72) Inventor: Adam Leon Kesner, Denver, CO (US)

(73) Assignee: Memorial Sloan Kettering Cancer Center, New York, NY (US)

(*) Notice: Subject to any disclaimer, the term of this patent is extended or adjusted under 35 U.S.C. 154(b) by 0 days.

(21) Appl. No.: 14/773,759

(22) PCT Filed: Mar. 12, 2014

(86) PCT No.: PCT/IL2014/050255
§ 371 (c)(1),
(2) Date: Sep. 9, 2015

(87) PCT Pub. No.: WO2014/141256
PCT Pub. Date: Sep. 18, 2014

(65) Prior Publication Data
US 2016/0019679 A1    Jan. 21, 2016

Related U.S. Application Data

(60) Provisional application No. 61/781,031, filed on Mar. 14, 2013.

(51) Int. Cl.
*G06T 5/00*    (2006.01)
*G06K 9/40*    (2006.01)
(Continued)

(52) U.S. Cl.
CPC .............. *G06T 5/002* (2013.01); *G06K 9/40* (2013.01); *G06T 5/10* (2013.01); *G06T 7/11* (2017.01);
(Continued)

(58) Field of Classification Search
None
See application file for complete search history.

(56) References Cited

U.S. PATENT DOCUMENTS 5,415,171 A * 5/1995 Goh .................. A61B 8/08
                                              600/443
6,086,537 A    7/2000 Urbano et al.
(Continued)

FOREIGN PATENT DOCUMENTS

WO    9946731    9/1999

OTHER PUBLICATIONS

International Search Report for PCT/IL2014/050255 dated Aug. 24, 2014.
(Continued)

*Primary Examiner* — Delomia L Gilliard
(74) *Attorney, Agent, or Firm* — Foley & Lardner LLP; Shabbi S. Khan

(57) ABSTRACT

A method of providing a medical image of a region of interest (ROI) of a patient, the method comprising: acquiring a time ordered sequence of measurements of radiation used to provide the medical image; generating a Fourier transform of the time ordered sequence or a function thereof; using the Fourier transform to determine which of the frequencies characterize real motion of tissue in the ROI and which characterize noise; generating a corrected Fourier transform that is exclusive of frequencies that characterize noise; and providing a medical image of the ROI using the corrected Fourier transform.

7 Claims, 2 Drawing Sheets

(51) Int. Cl.
  *G06T 5/10*   (2006.01)
  *G06T 7/11*   (2017.01)
  *G06T 7/262*  (2017.01)
  *A61B 6/03*   (2006.01)

(52) U.S. Cl.
  CPC .............. *G06T 7/262* (2017.01); *A61B 6/037* (2013.01); *G06T 2207/10104* (2013.01); *G06T 2207/10108* (2013.01); *G06T 2207/20056* (2013.01)

(56) References Cited

U.S. PATENT DOCUMENTS

| | | |
|---|---|---|
| 6,144,874 A | 11/2000 | Du |
| 6,298,260 B1 | 10/2001 | Sontag |
| 6,501,981 B1 | 12/2002 | Schweikard |
| 6,539,074 B1 | 3/2003 | Yavuz |
| 6,556,695 B1 | 4/2003 | Packer |
| 7,359,535 B2 | 4/2008 | Salla |
| 7,734,078 B2 | 6/2010 | Prince |
| 7,756,307 B2 | 7/2010 | Thielemans |
| 2004/0218794 A1 | 11/2004 | Kao |
| 2005/0123183 A1* | 6/2005 | Schleyer ............... G06T 5/20 382/131 |
| 2007/0081704 A1 | 4/2007 | Pan |
| 2007/0106149 A1 | 5/2007 | Mistretta |
| 2007/0127797 A1 | 6/2007 | Angelos |
| 2007/0237372 A1 | 10/2007 | Chen |
| 2008/0080786 A1* | 4/2008 | Mitchell ............ G01R 33/4806 382/280 |
| 2008/0219535 A1 | 9/2008 | Mistretta et al. |
| 2008/0226149 A1 | 9/2008 | Wischmann |
| 2009/0076369 A1 | 3/2009 | Mistretta |
| 2009/0290774 A1 | 11/2009 | Shechter |
| 2009/0299184 A1 | 12/2009 | Walker |
| 2010/0183206 A1 | 7/2010 | Carlsen |
| 2014/0031688 A1* | 1/2014 | Perrey ...................... A61B 8/54 600/443 |

OTHER PUBLICATIONS

Michael A. King "Use of a Nonstationary Temporal Wiener Filter in Nuclear Medicine" Department of Nuclear Medicine, University of Massachusetts Medical School, Worcester, Massachusetts, USA, 4 pps.

* cited by examiner

MEDICAL IMAGING

RELATED APPLICATIONS

The present application is a US National Phase of PCT Application No. PCT/IB2014/050255, filed on Mar. 12, 2014, which claims the benefit under 35 U.S.C. §119(e) of U.S. Provisional Application 61/781,031 filed on Mar. 14, 2013 the disclosure of which is incorporated herein by reference.

TECHNICAL FIELD

Embodiments of the invention relate to medical imaging.

BACKGROUND

Various methods, "modalities", for imaging internal features of a region of interest (ROI) of a person's body for diagnostic purposes are known. Among the imaging modalities are by way of example, the familiar X-ray and ultrasound (US) imaging modalities, computerized tomography (CT), magnetic resonance imaging (MRI), and the nuclear medicine imaging techniques referred to as positron emission tomography (PET) and single photon emission computerized tomography (SPECT).

All of the various modalities employ sensors that receive and register amounts of radiation, hereinafter also referred to as "imaging radiation", that is reflected or emitted by the features, transmitted through the features, or emitted by substances located in the features. Imaging radiation may for example comprise, X-rays (CT imaging), γ-ray photons (PET and SPECT imaging), radio frequency (RF) electromagnetic waves (MRI) and ultrasound (US imaging). The amounts of imaging radiation from the ROI that are registered by the sensors and associated with each of a plurality of voxels in the ROI are used to provide an image of the patient's features in the ROI.

By way of example, PET scans of a ROI of a patient are produced by introducing a biologically active "carrier" molecule that is tagged with a positron emitting radionuclide into the patient's body. The molecule concentrates in various regions of the ROI depending on features in the ROI and a type of biological activity that characterizes the carrier molecule. Positrons emitted by the radionuclide in voxels of the ROI at which the molecule concentrates annihilate with electrons in the voxels and produce pairs of "back-to-back" photons that propagate out of the voxels and the patient's body along opposite, collinear directions. A PET scanner comprising sensors that detect pairs of back-to-back photons leaving the patient's body determines from which voxels in the body the back-to-back photons originate to map the concentration of the molecule in the body. The concentration map shows which features in the ROI preferentially accumulate the molecule and may be used to image the features, characterize their morphology and/or metabolic functioning. PET imaging is often used to locate and image cancerous growths in a patient's body.

The various medical imaging modalities are subject in varying degree to motion blurring, which degrades sharpness of images the modalities provide. The longer an exposure period a given medical imaging modality requires to sense and register a sufficient amount of imaging radiation to acquire a satisfactory image of a patient, the more sensitive the modality is to blurring resulting from motion of the patient during the exposure period. Besides "fidget" motion of a patient during an exposure period, which may be subject to a satisfactory degree of control, relatively difficult or impossible to control motion of body organs that accompany the respiratory and cardiac cycles of the patient contribute to motion blurring. In particular, PET or SPECT, which require relatively long exposure periods because the flux of imaging radiation (γ-ray photons) that they image is typically relatively weak, are sensitive to motion blurring.

Various windowing techniques have been developed to compensate a medical imaging modality for motion blurring in an image it acquires of a patient that is caused by motion accompanying the patient's cardiac or respiratory cycles. Generally, the windowing techniques divide an exposure period during which the modality registers imaging radiation into a plurality of relatively short duration "imaging windows", for each of which an amount of the imaging radiation is measured. The imaging windows are configured so that during the exposure period there are a same whole number "N" of imaging windows for each of the patient's cardiac or respiratory cycle. The imaging windows are phase synchronized to the cycles so that every N-th window in the plurality of windows corresponds to substantially a same phase of the cycles. Configuring the imaging windows so that there are N imaging windows per cycle and that the imaging windows are phase synchronized is typically done by monitoring the cardiac or respiratory cycles with a motion sensor to sense phases of the cycles and when the cycles begin and end. Measurements of imaging radiation are labeled with cycle phases that are simultaneous with times at which the measurements are made and the phase labeled measurements are processed responsive to their respective associated phase labels to bin the measurements in phase synchronized windows.

Amounts of imaging radiation registered during imaging windows corresponding to a same given phase of the cardiac or respiratory cycle may be added, and the summed amount of imaging radiation is used to provide an image, hereinafter also referred to as a "phase image" of the patient's features for the given phase of the cycle. A phase ordered sequence of phase images, acquired for a ROI of a patient for different phases of the cycle may be used to provide a motion picture of the patient's features in the ROI that show how the features move during the cardiac or respiratory cycle.

Phase images of the features of an ROI are expected to have improved sharpness because feature displacement caused by cardiac or respiratory motion during the imaging windows is limited due to the relatively short duration of the windows. It is noted however, that whereas duration of the imaging windows, and as a result motion blur in phase images, decreases with increase in N, statistical, "shot noise", increases with increase in N. If N is too small, shot noise may offset gains in image blur and degrade phase images to a degree at which the image is no longer satisfactory.

SUMMARY

An aspect of an embodiment of the invention relates to providing a method for acquiring a medical image of a ROI in a patient using a windowed imaging modality that reduces background noise in the image.

According to an embodiment of the invention, measurements of windowed amounts of imaging radiation acquired in accordance with an imaging modality for the patient's ROI are processed to determine which frequencies characterize time development of the imaging radiation as a function of time, or of phase of the cardiac or respiratory cycles of the patient. Frequencies that characterize the time or phase development due to real motion of tissue in the ROI and frequencies that characterize noise are distinguished. Substantially only frequencies that are distinguished as characterizing real motion are used to generate medical images for the ROI. A medical image may be a spatial image that provides a picture of the ROI at a given time, or phase of a cardiac or respiratory cycle, or a representation, such as a sinogram, of measurements of imaging radiation as a function of time or cycle phase that may be used for diagnosing a medical condition of the patient.

A method of acquiring a medical image may comprise: acquiring a time ordered sequence of measurements of amounts of imaging radiation used to provide the medical image for, optionally, each of a plurality of voxels in the ROI; windowing the measurements acquired for each voxel in a sequence of a same number N of imaging windows for each of the patient's cardiac or respiratory cycle, that are synchronized with phases of the cycle; adding amounts of imaging radiation measured for each voxel from imaging windows synchronized with a same phase of a cycle to provide a discrete, function, hereinafter a "phase synchronized function", of the imaging radiation as a function of cycle phase for the voxel; adding measurements of amounts of imaging radiation for the voxel from randomly selected imaging windows to provide a discrete, "random function" of the imaging radiation for the voxel; Fourier transforming the synchronized and random functions for each voxel; determining for which frequencies in the Fourier transforms of the synchronized and random functions frequency amplitudes exhibit a statistically significant difference and to which extent; generating a corrected Fourier transform for the synchronized Fourier transform that comprises frequencies with amplitudes altered to reflect the degree in which the random and synchronized signals are significantly differentiated; and inverse Fourier transforming the corrected Fourier transform to generate a phase, or time, dependent image of the voxel.

In the discussion, unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the description and claims is considered to be the inclusive "or" rather than the exclusive or, and indicates at least one of, or any combination of items it conjoins.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF FIGURES

Non-limiting examples of embodiments of the invention are described below with reference to figures attached hereto that are listed following this paragraph. Identical structures, elements or parts that appear in more than one figure are generally labeled with a same numeral in all the figures in which they appear. Dimensions of components and features shown in the figures are chosen for convenience and clarity of presentation and are not necessarily shown to scale.

DETAILED DESCRIPTION

Figure 1:
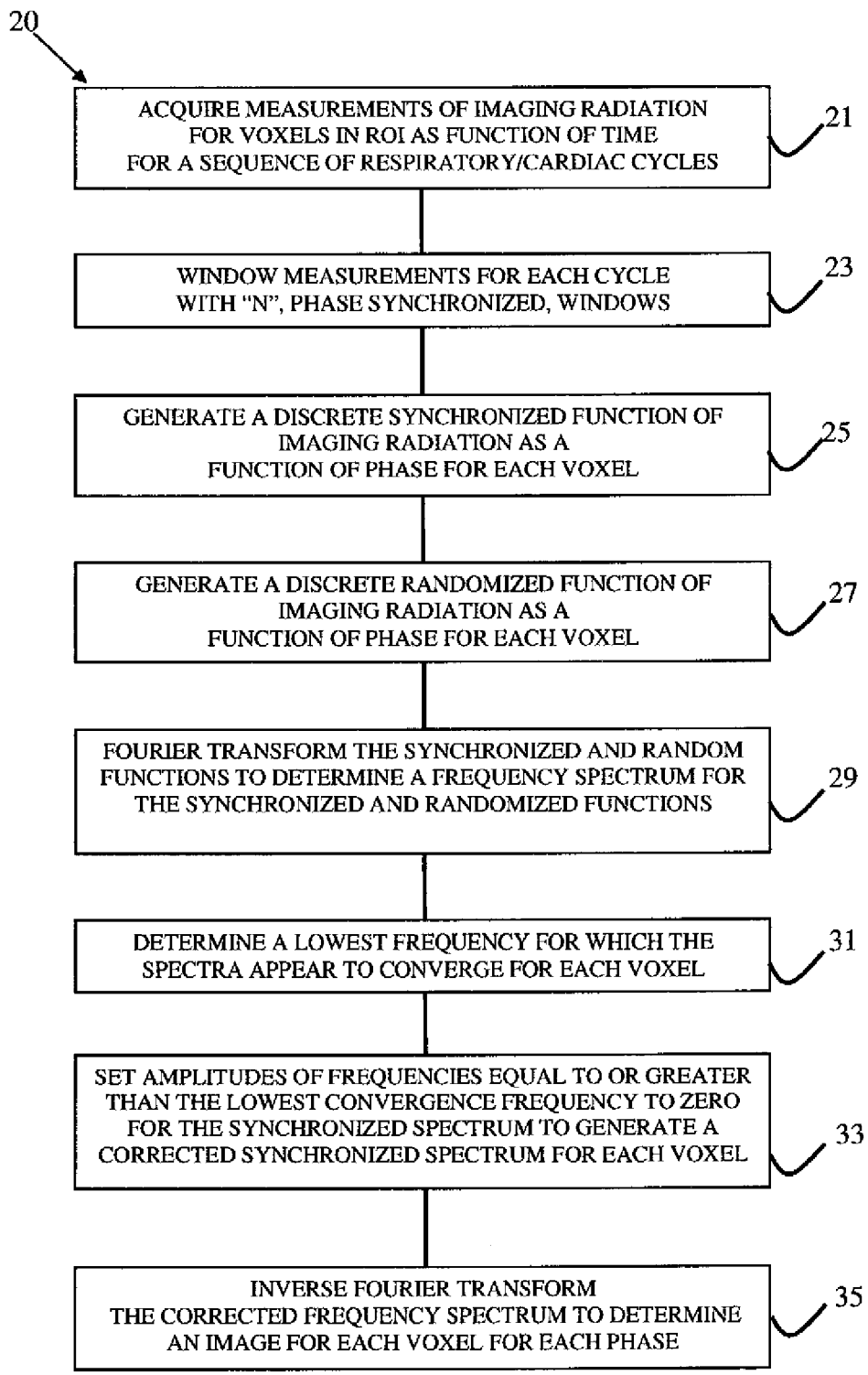
FIG. 1 shows a flow diagram of a method of providing a medical image by windowing imaging radiation data acquired by a medical imaging modality, in accordance with an embodiment of the invention.

FIG. 1 shows a flow diagram of a method 20 of acquiring a medical image of a ROI of a patient using a suitable imaging modality by windowing time dependent measurements of amounts of imaging radiation registered by apparatus appropriate for implementing the modality. By way of example, it is assumed that the imaging modality is PET and windowing is preformed to moderate image blurring due to respiratory motion.

In a block 21 measurements of imaging radiation, which in the case of PET comprise measuring emission flux of pairs of back-to-back γ-ray photons, are acquired by PET apparatus during a sequence of a patient's respiratory cycles for each of a plurality of voxels of a ROI of the patient as a function of time.

Measurements as a function of time may be made by tagging each event with an event time at which the event was registered. In a block 23 the registered and time tagged events are optionally grouped responsive to their respective event times into a same number of "N" imaging windows for each respiratory cycle. The N imaging windows are synchronized with N "discrete phases" of the cycle so that every N-th imaging window is substantially simultaneous with a same discrete phase of a different respiratory cycle. Optionally, phases of the respiratory cycles are determined from the tagged events by processing time dependence of the events to determine respiratory frequencies that characterize the patient's respiration. The respiratory frequencies are used to define the discrete phases and the correspondence of the event times with the discrete phases.

In an embodiment of the invention, in a block 25 a discrete synchronized function of the imaging radiation as a function of respiratory phase is defined, optionally, for each voxel in the ROI. The function has a value for each of a sequence of N consecutive discrete phases of a respiratory cycle that is equal to a sum of measurements of imaging radiation acquired for the voxel for each of a plurality of imaging windows corresponding to the discrete phase. Optionally, in a block 27 a discrete randomized function of the imaging radiation as a function of respiratory phase is defined for each voxel in the ROI. The randomized function has a value for each of the sequence of N consecutive discrete phases of a respiratory cycle that is equal to a sum of measurements of imaging radiation acquired for the voxel for each of a plurality of randomly chosen imaging windows.

Figure 2A:
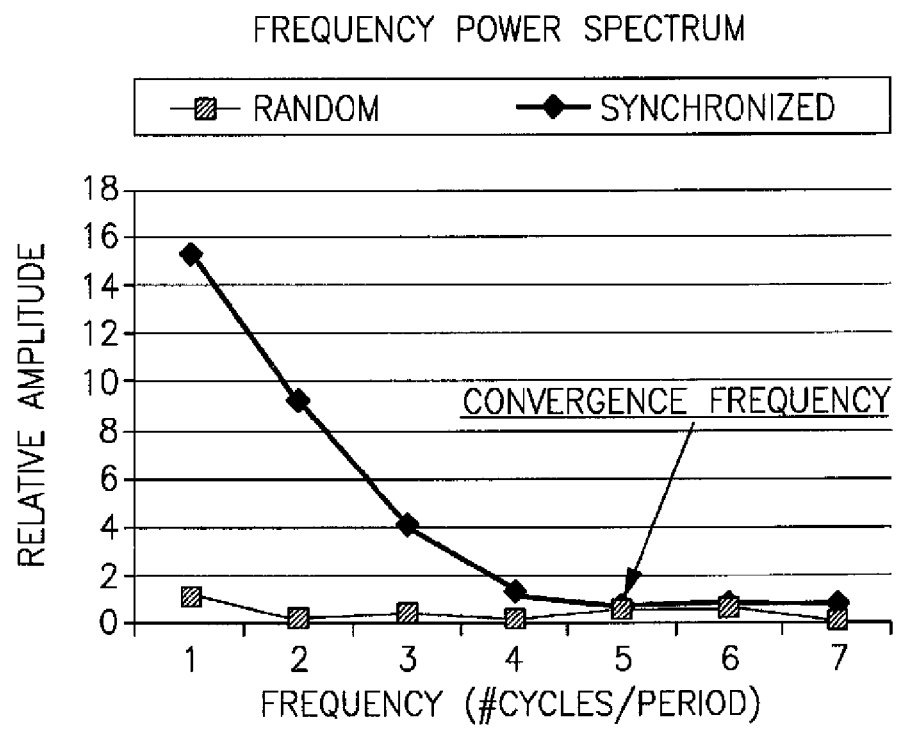
FIGS. 2A-2B show schematic graphs of imaging radiation data that illustrate features of the flow diagram shown in FIG. 1, in accordance with an embodiment of the invention.

In a block 29 the synchronized and randomized functions are Fourier transformed to provide a frequency spectrum for each of the functions for each voxel. Optionally, in a block 31 the frequency spectra of the functions are compared to determine a lowest frequency for which the frequency spectra may be considered to converge. In an embodiment of the invention the lowest "frequency of convergence" is a lowest frequency for which the amplitudes of the frequency in the synchronized and randomized functions of imaging radiation for the voxel may be considered substantially the same in accordance with a suitable statistical criterion. FIG. 2A shows schematic frequency spectra for synchronized and randomized intensity functions and a lowest frequency of convergence, labeled "convergence frequency", for the spectra.

Figure 2B:
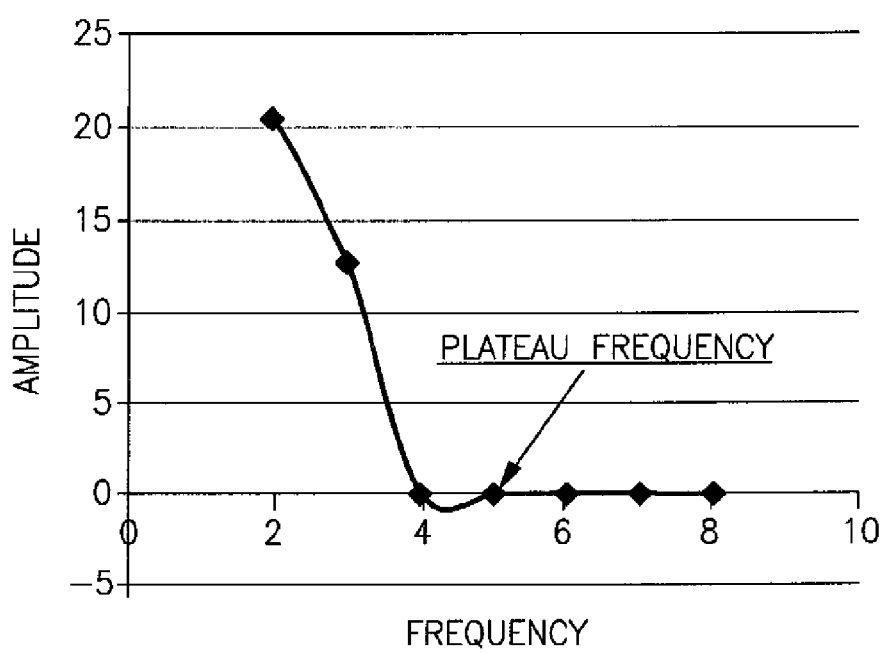

In an embodiment of the invention a lowest frequency of convergence is determined from the frequency spectrum of the synchronized intensity function as a lower bound frequency at which the frequency amplitudes of synchronized frequency spectrum appears to plateau to a minimum. FIG. 2B shows schematic synchronized frequency spectrum and a lower bound frequency, labeled "plateau frequency", at which the spectrum appears to plateau to a minimum.

In a block 33 amplitudes of frequencies equal to or greater than the lowest convergence frequency or plateau frequency are set equal to zero in the frequency spectrum for the synchronized intensity spectrum to generate a corrected synchronized frequency spectrum. In a block 35 the corrected frequency spectrum for the voxel is used to generate an image of the voxel for each of the N discrete phases of the respiration cycle.

In an embodiment of the invention, a quality of image (QoI) index is provided for the image. The QoI may be a function of information comprised in the synchronized and, optionally, in the randomized frequency spectrum. Optionally, the QoI comprises a ratio equal to a sum of the absolute values of the fundamental frequency of the synchronized frequency spectra for a plurality of voxels in the ROI divided by a sum of the absolute values of the amplitudes of a harmonic frequency of the frequency spectra for which the sum is a minimum.

It is noted that whereas in the above example, the medical image was assumed to be a picture of an ROI of a patient, and a corrected frequency spectrum was generated for each of a plurality of voxels in the ROI, practice of the invention is not limited to medical images for which corrected frequency spectra are generated for voxels in the ROI. For example, global synchronized and randomized functions of the imaging radiation and their discrete Fourier transforms may be generated for an ROI that is not partitioned into voxels. The Fourier transforms may be used to generate a global corrected Fourier transform which is used to provide a sinogram for the ROI.

It is further noted that given a corrected Fourier transform, a substantially continuous movie of an image of an ROI as a function of phase or time may be generated by repeatedly, incrementally shifting the phases of the components of the corrected Fourier transform and following each incremental phase shift, inverse Fourier transforming the incrementally phase shifted Fourier transform.

In the description and claims of the present application, each of the verbs, "comprise" "include" and "have", and conjugates thereof, are used to indicate that the object or objects of the verb are not necessarily a complete listing of components, elements or parts of the subject or subjects of the verb.

Descriptions of embodiments of the invention in the present application are provided by way of example and are not intended to limit the scope of the invention. The described embodiments comprise different features, not all of which are required in all embodiments of the invention. Some embodiments utilize only some of the features or possible combinations of the features. Variations of embodiments of the invention that are described, and embodiments of the invention comprising different combinations of features noted in the described embodiments, will occur to persons of the art. The scope of the invention is limited only by the claims.

The invention claimed is:

1. A method of providing a medical image of a region of interest (ROI) of a patient, the method comprising:
acquiring a time ordered sequence of measurements of radiation used to provide the medical image;
generating a Fourier transform of the time ordered sequence or a function thereof;
using the Fourier transform to determine which of the frequencies characterize real motion of tissue in the ROI and which characterize noise;
generating a corrected Fourier transform that is exclusive of frequencies that characterize noise; and
providing a medical image of the ROI using the corrected Fourier transform.

2. The method according to claim 1 wherein determining which of the frequencies characterize real motion of tissue comprises determining a lowest frequency that bounds a region at which the spectrum exhibits a plateau.

3. The method according to claim 1 wherein a function of the time ordered sequence comprises a function of the measurements windowed in a sequence of imaging windows that are synchronized with phases of the patient's cardiac or respiratory cycle.

4. The method according to claim 1 wherein Fourier transforming the function comprises Fourier transforming the windowed function to provide a spectrum of frequencies as a function of phase of cardiac or respiratory cycle.

5. The method according to claim 1 wherein providing a medical image comprises inverse Fourier transforming the corrected Fourier transform.

6. A method of providing a medical image of a region of interest (ROI) of a patient, the method comprising:
acquiring a time ordered sequence of measurements of amounts of imaging radiation used to provide the medical image for each of a plurality of voxels in the ROI;
windowing the measurements acquired for each voxel in a sequence of imaging windows that are synchronized with phases of the patient's cardiac or respiratory cycle;
adding measurements for each voxel from imaging windows synchronized with a same phase of the cycle to provide a discrete, synchronized function of the imaging radiation for the voxel;
adding intensity measurements for the voxel from randomly selected imaging windows to provide a discrete random function of the imaging radiation for the voxel;
Fourier transforming the synchronized and random functions for each voxel;
determining which frequencies in the Fourier transforms of the synchronized and random functions exhibit a difference below a predetermined threshold in their respective amplitudes;
providing a corrected synchronized Fourier transform by excluding frequencies in the synchronized Fourier transform that exhibit a difference below a predetermined threshold in their respective amplitudes; and
inverse Fourier transforming the corrected Fourier transform to generate a time dependent image of the voxel.

7. A method of providing a medical image of a region of interest (ROI) of a patient, the method comprising:
acquiring a time ordered sequence of measurements of radiation used to provide the medical image;
generating a Fourier transform of the time ordered sequence or a function thereof;
using the Fourier transform to determine which of the frequencies characterize real motion of tissue in the ROI and which characterize noise by identifying frequencies in a plateau region of the spectrum and associating the frequencies in the plateau region with noise;
generating a corrected Fourier transform that is exclusive of frequencies, or portions of frequencies, that are associated with noise; and
providing a medical image of the ROI using the corrected Fourier transform.

* * * * *